United States Patent
Liu et al.

(10) Patent No.: US 11,680,077 B2
(45) Date of Patent: Jun. 20, 2023

(54) PREPARATION METHOD FOR GLUFOSINATE

(71) Applicants: LIER CHEMICAL CO., LTD., Sichuan (CN); GUANGAN LIER CHEMICAL CO., LTD., Sichuan (CN)

(72) Inventors: Yongjiang Liu, Sichuan (CN); Lei Zhou, Sichuan (CN); Wei Zeng, Sichuan (CN); Min Xu, Sichuan (CN); Ke Cheng, Sichuan (CN); Yingsui Yin, Sichuan (CN)

(73) Assignees: LIER CHEMICAL CO., LTD., Sichuan (CN); GUANGAN LIER CHEMICAL CO., LTD., Sichuan (CN)

( * ) Notice: Subject to any disclaimer, the term of this patent is extended or adjusted under 35 U.S.C. 154(b) by 92 days.

(21) Appl. No.: 17/610,051

(22) PCT Filed: Jan. 20, 2021

(86) PCT No.: PCT/CN2021/072854
§ 371 (c)(1),
(2) Date: Nov. 9, 2021

(87) PCT Pub. No.: WO2021/147894
PCT Pub. Date: Jul. 29, 2021

(65) Prior Publication Data
US 2022/0259232 A1  Aug. 18, 2022

(30) Foreign Application Priority Data
Jan. 20, 2020 (CN) .......................... 202010064268.7

(51) Int. Cl.
*C07F 9/30* (2006.01)
(52) U.S. Cl.
CPC .................. *C07F 9/301* (2013.01)
(58) Field of Classification Search
CPC .... C07F 9/301; C07F 9/30; C07F 9/32; C07F 9/4866; C07F 9/4891; C07F 9/52; C07C 271/22
See application file for complete search history.

(56) References Cited

U.S. PATENT DOCUMENTS 5,442,088 A * 8/1995 Hoffmann ............. C07C 311/19
560/150

FOREIGN PATENT DOCUMENTS

| CN | 106083922 B | 8/2018 |
|---|---|---|
| CN | 109232644 A | 1/2019 |
| SU | 165724 A | 10/1964 |
| WO | 2021/143712 A1 | 7/2021 |
| WO | 2021/143713 A1 | 7/2021 |

OTHER PUBLICATIONS

Abraham et al. (Redistribution, Condensation, and Rearrangement Reactions Involving Dichloro- and Dimethoxymethylphosphines, Inorganic Chemistry, vol. 13, No. 10, pp. 2346-2350 Published 1974. (Year: 1974).*
Registry. "RN: 41157-33-9, etc." ACS on STN, Nov. 16, 1984.
Weissermel, Klaus et al., "Advances in Organophosphorus Chemistry Based on Dichloro(methyl)phosphane," Angew. Chem. Int. Ed. Engl., vol. 20, Dec. 31, 1981, pp. 223-233.
Xu, Xue Song et al., "A Facile Synthetic Route to L-Phosphinothricin," Chinesse Chemical Letters, vol. 17, No. 2, Dec. 31, 2006, pp. 177-179.
Samuels, M.C. et al., "Solid-Phase Synthesis and Catalytic Screening of Polystyrene Supported Diphosphines," Top Catal., vol. 59, Aug. 25, 2016, pp. 1793-1799.
Registry. "RN: 51934-18-6, etc." ACS on STN, Nov. 16, 1984.
Registry. "RN: 1257864-98-4" ACS on STN, Dec. 29, 2010.
International Search Report in International Application No. PCT/CN2021/072854 (dated Apr. 2021).
Communication Pursuant to Article 94(3) EPC in European Application No. 21743682.3 (dated Oct. 2022).
Supplementary International Search Report in International Application No. PCT/CN2021/072854 (dated Jun. 2022).
First Examination Report in Australian Application No. 2021209728 (dated Jun. 2022).

(Continued)

*Primary Examiner* — Yevgeny Valenrod
*Assistant Examiner* — Blaine G Doletski
(74) *Attorney, Agent, or Firm* — Venable LLP

(57) ABSTRACT

A preparation method for glufosinate or a salt thereof, an enantiomer thereof, or mixtures of the enantiomer thereof in all ratios, comprising reacting a compound of formula (II) or a salt, an enantiomer, or mixtures of the enantiomer in all ratios with one or more compounds of formula (III) or mixtures thereof.

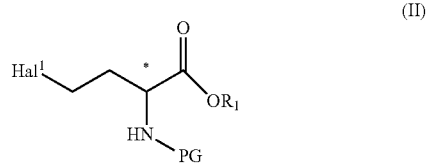

(II)

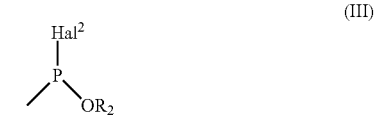

(III)

31 Claims, No Drawings

(56) References Cited

OTHER PUBLICATIONS

Bayer et al., "Stoffwechselprodukte von Mikroorganismen. 98. Mitteilung. Phosphinothricin und Phosphinothricyl-Alanyl-Alanin," Helvetica Chimica Acta, vol. 55, No. 1, pp. 224-239 (1972).

Weissermel et al., "Advances in Organophosphorus Chemistry Based on Dichloro(methyl)phosphane," Angewandte Chemie Int'l Ed., vol. 20, No. 3, pp. 223-233 (1981).

Abraham et al., "Redistribution, Condensation, and Rearrangement Reactions Involving Dichloro- and Dimethoxymethylphosphines," Inorganic Chemistry, vol. 13, No. 10, pp. 2346-2350 (1974).

Shi et al., "Synthesis of MeP(OEt)2—An Intermediate of Glufosinate," Jiangsu Chemical Industry, vol. 33 Suppl., pp. 106-107 (2005).

Steininger, "Über Phosphonigsäure-monoester-monochloride," Chemische Berichte, vol. 95, No. 12, pp. 2993-2996 (1962).

First Office Action in Chinese Application No. 202180002115.2 (dated Dec. 2021).

First Office Action in Israeli Application No. 292593 (dated Aug. 2022).

First Office Action in Canadian Application No. 3,157,884 (dated Jul. 2022).

Technical Examination Report in Brazilian Application No. 112022008792-6 (dated Dec. 2022).

First Substantive Requirement in Mexican Application No. MX/a/2022/005442 (dated Jan. 2023).

Second Office Action in Canadian Application No. 3,157,884 (dated Jan. 2023).

Notice of Reasons for Refusal in Japanese Application No. 2022-534422 (dated Jan. 2023).

Notification of Preliminary Rejection in Korean Application No. 10-2022-7017101 (dated Dec. 2022).

\* cited by examiner

PREPARATION METHOD FOR GLUFOSINATE

TECHNICAL FIELD

The present invention relates to a preparation method for glufosinate.

BACKGROUND ART

Glufosinate is an important herbicide.

CONTENTS OF THE INVENTION

The present invention provides a method for preparing glufosinate of formula (I) or a salt, an enantiomer thereof or a mixture of the enantiomers in all ratios, comprising the following steps:

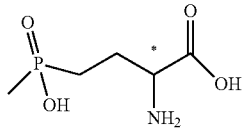
(I)

a) reacting a compound of formula (II) or a salt, an enantiomer thereof or a mixture of the enantiomers in all ratios,

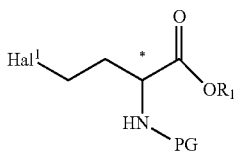
(II)

with one or more compounds of formula (III) or a mixture;
the above mixture being a mixture comprising one or more compounds of formula (IV) and one or more compounds of formula (V); or a mixture comprising one or more compounds of formula (IV) and one or more compounds of formula (III); or a mixture comprising one or more compounds of formula (V) and one or more compounds of formula (III); or a mixture comprising one or more compounds of formula (III), one or more compounds of formula (IV) and one or more compounds of formula (V);

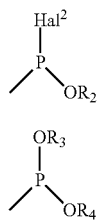
(III)

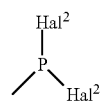
(IV)

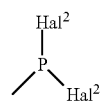
(V)

b) reacting the intermediate, no matter whether it is isolated or not, in the presence of water and an acid or a base to obtain the glufosinate (I) or a salt, an enantiomer thereof or a mixture of the enantiomers in all ratios;
wherein when PG is an amino protecting group, a step of removing the amino protecting group can be further comprised;
wherein $Hal^1$ and $Hal^2$ are each independently halogen; PG is hydrogen or an amino protecting group; $R_1$, $R_2$, $R_3$ and $R_4$ are each independently alkyl, phenyl or substituted phenyl, and when the mixture comprises the mixture of one or more compounds of formula (IV) and one or more compounds of formula (III), or when the mixture comprises the mixture of one or more compounds of formula (III), one or more compounds of formula (IV) and one or more compounds of formula (V), $R_2$ is either $R_3$ or $R_4$; and the chiral carbon atom is labeled with *.

The present invention further provides a method for preparing enantiomerically pure glufosinate of formula (I) or a salt thereof,

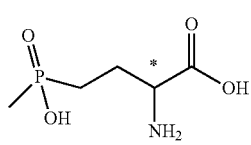
(I)

the method comprises the following steps:
a1) reacting an enantiomerically pure compound of formula (II) or a salt thereof,

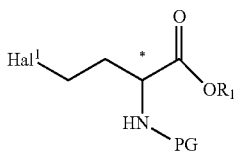
(II)

with a compound of formula (III),

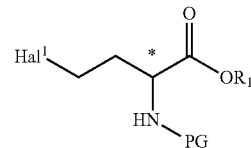
(III)

or one or more compounds of formula (III) or a mixture;
the above mixture being a mixture comprising one or more compounds of formula (IV) and one or more compounds of formula (V); or a mixture comprising one or more compounds of formula (IV) and one or more compounds of formula (III); or a mixture comprising one or more compounds of formula (V) and one or more compounds of formula (III); or a mixture comprising one or more compounds of formula (III), one or more compounds of formula (IV) and one or more compounds of formula (V);

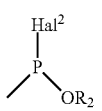
(III)

-continued

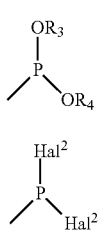

(IV)

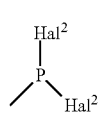

(V)

b1) reacting the intermediate, no matter whether it is isolated or not, in the presence of water and an acid or a base to obtain the enantiomerically pure glufosinate (I) or a salt thereof;

wherein when PG is an amino protecting group, a step of removing the amino protecting group can be further comprised;

wherein $Hal^1$ and $Hal^2$ are each independently halogen; PG is hydrogen or an amino protecting group; $R_1$, $R_2$, $R_3$ and $R_4$ are each independently alkyl, phenyl or substituted phenyl, and when the mixture comprises the mixture of one or more compounds of formula (IV) and one or more compounds of formula (III), or when the mixture comprises the mixture of one or more compounds of formula (III), one or more compounds of formula (IV) and one or more compounds of formula (V), $R_2$ is either $R_3$ or $R_4$; and the chiral carbon atom is labeled with *.

In certain specific embodiments, one compound of formula (III), e.g., chloro(ethoxy)(methyl)phosphane, is employed.

In certain specific embodiments, a mixture of one compound of formula (IV) and one compound of formula (V) is employed, such as a mixture of dichloro(methyl)phosphane and diethyl methylphosphonite, and the mixture can be further added with a compound of formula (III), e.g., chloro(ethoxy)(methyl)phosphane, in any ratio.

Further, the enantiomeric ratio is (L):(D)-enantiomer or (D):(L)-enantiomer of 50.5:49.5 to 99.5:0.5.

Further, the enantiomeric ratio is (L):(D)-enantiomer of 50.5:49.5 to 99.5:0.5.

Further, the PG is hydrogen.

Further, the $Hal^1$ is a chlorine atom.

Further, the $Hal^2$ is a chlorine atom.

Further, the $R_1$, $R_2$, $R_3$ and $R_4$ are each independently $C_1$-$C_6$ alkyl, preferably $C_1$-$C_4$ alkyl.

Further, the $R_1$ is ethyl.

Further, the $R_2$ is ethyl.

Further, the $R_3$ is ethyl.

Further, the $R_4$ is ethyl.

In certain specific embodiments, the mixture is a mixture of one or more compounds of formula (IV) and one or more compounds of formula (III), and the molar ratio of the compounds of formula (IV) to the compounds of formula (III) is (0.9-1.1):1 or (0.05-1.1):1; or the mixture is a mixture of one or more compounds of formula (V) and one or more compounds of formula (III), and the molar ratio of the compounds of formula (V) to the compounds of formula (III) is (0.9-1.1):1 or (0.05-1.1):1; or the mixture is a mixture comprising one or more compounds of formula (IV) and one or more compounds of formula (V), and the molar ratio of the compounds of formula (IV) to the compounds of formula (V) is (0.9-1.1):1.

Further, in aforementioned step a) or a1), the reaction can proceed at room temperature, the reaction temperature can be 20-200° C., and preferably 90-140° C. in consideration of reaction efficiency.

Further, the aforementioned step a) or a1) is carried out in the presence of a base.

Further, the base in aforementioned step a) or a1) is an organic base or ammonia.

Further, in aforementioned step a) or a1), the organic base is selected from the group consisting of an organic amine, pyridine or a pyridine derivative having 1-3 substituents attached to one or more carbon atoms in the heterocycle, piperidine or a piperidine derivative having 1-3 substituents attached to one or more carbon atoms in the heterocycle.

Further, the organic base is selected from the group consisting of triethylamine, piperidine or pyridine.

Further, in aforementioned step a) or a1), the molar ratio of the base to the total amounts of the compound of formula (III) and the compound of formula (V) is (1-10):1.

Further, in aforementioned step a) or a1), the reaction is carried out under a solvent-free condition or in an inert solvent.

Further, in aforementioned step a) or a1), the inert solvent is selected from any one or more of benzene solvents, amide solvents, hydrocarbon solvents, halogenated hydrocarbon solvents, sulfone or sulfoxide solvents, ether solvents or ester solvents; preferably, the inert solvent is selected from any one or more of benzene solvents, amide solvents, halogenated hydrocarbon solvents, ether solvents or ester solvents.

Further, in aforementioned step a) or a1), the inert solvent is selected from any one or more of chlorobenzene, trimethylbenzene, 1,4-dioxane, 1,2-dichloroethane, dimethyl sulfoxide, N-methylpyrrolidone, N,N-dimethylformamide, petroleum ether, n-heptane, tetrahydrofuran, methyltetrahydrofuran, benzene, toluene, ethyl acetate, and butyl acetate.

Further, in aforementioned step a) or a1), the molar ratio of the compound of formula (III) or the mixture to the compound of formula (II) is 1:(0.8-10), preferably 1:(1-3); or the molar ratio of the compound of formula (II) to the compound of formula (III) or the mixture is 1:(0.8-10), preferably 1:(1-3).

Further, in aforementioned step b) or b1), an inorganic acid or an organic acid is added.

Further, the inorganic acid is hydrochloric acid or sulfuric acid.

Further, in aforementioned step b) or b1), the base is an inorganic base or an organic base.

Further, the base is alkali metal hydroxide, alkali-earth metal hydroxide, alkali metal carbonate, alkali-earth metal carbonate, alkali metal bicarbonate or alkali-earth metal bicarbonate.

Further, the base is NaOH, KOH or Ba(OH)$_2$.

Further, in aforementioned step b) or b1), the reaction temperature is 20-150° C.

As a specific embodiment, a compound of formula (IIa) is reacted with a compound of formula (IIIa),

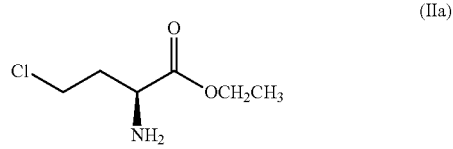

(IIa)

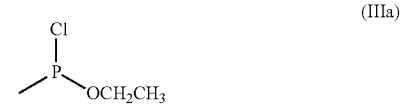

(IIIa)

and an acid (e.g., hydrochloric acid) is then added to obtain L-glufosinate.

The present invention further provides a compound of formula (III)

(III)

wherein Hal² and R₂ are as defined above.

The present invention further provides use of the compound of formula (III), particularly a compound of formula (IIIa), in the preparation of glufosinate or a salt thereof, or L-glufosinate or a salt thereof,

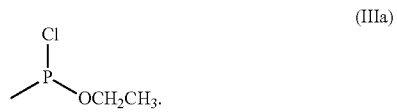
(IIIa)

The present invention further provides a mixture comprising one or more compounds of formula (IV) and one or more compounds of formula (V); or a mixture comprising one or more compounds of formula (IV) and one or more compounds of formula (III); or a mixture comprising one or more compounds of formula (V) and one or more compounds of formula (III); or a mixture comprising one or more compounds of formula (III), one or more compounds of formula (IV) and one or more compounds of formula (V);

(III)

(IV)

(V)

wherein Hal², R₂, R₃ and R₄ are as defined above.

Further, the above mixture is a mixture comprising one or more compounds of formula (IV) and one or more compounds of formula (V), and the molar ratio of the compounds of formula (IV) to the compounds of formula (V) is (0.9-1.1):1; or the mixture is a mixture comprising one or more compounds of formula (IV) and one or more compounds of formula (III), and the molar ratio of the compounds of formula (IV) to the compounds of formula (III) is (0.9-1.1):1 or (0.05-1.1):1; or the mixture is a mixture comprising one or more compounds of formula (V) and one or more compounds of formula (III), and the molar ratio of the compounds of formula (V) to the compounds of formula (III) is (0.9-1.1):1 or (0.05-1.1):1.

Further, the compound of formula (IV) is diethyl methylphosphonite, and the compound of formula (V) is dichloro(methyl)phosphane.

The present invention further provides use of the aforementioned mixture in the preparation of glufosinate or a salt thereof, or L-glufosinate or a salt thereof.

The method of the present invention is particularly suitable for the preparation of glufosinate, and substantially reduces the steps of the existing preparation processes. In particular, in the preparation of L-glufosinate, the product can effectively maintain the ee value of the raw material. For example, when an enantiomerically pure raw material (e.g., the enantiomeric excess percentage (% ee) is greater than 90%) is employed, the enantiomeric excess percentage (% ee) of the prepared L-glufosinate is greater than e.g., 50%, 55%, 60%, 65%, 70%, 75%, 80%, 85%, 90% or 95%.

Unless otherwise specified, the terms used in the specification and claims have the following meanings.

The term "amino protecting group" refers to a group that can be attached to a nitrogen atom in an amino group to protect the amino group from participating the reaction and can be easily removed in the subsequent reactions. Suitable amino protecting groups include, but are not limited to, the following protecting groups:

carbamate group of formula —C(O)O—R, wherein R is methyl, ethyl, tert-butyl, benzyl, phenethyl, CH₂=CH—CH₂—, etc.; amide group of formula —C(O)—R', wherein R' is methyl, ethyl, phenyl, trifluoromethyl, etc.; N-sulfonyl derivative group of formula —SO₂—R", wherein R" is tolyl, phenyl, trifluoromethyl, 2,2,5,7,8-pentamethylchroman-6-yl-, 2,3,6-trimethyl-4-methoxybenzene, etc.

The term "alkyl" refers to a saturated aliphatic hydrocarbon group, including linear and branched groups having 1 to 18 carbon atoms. Alkyl having 1 to 6 carbon atoms, such as methyl, ethyl, propyl, 2-propyl, n-butyl, isobutyl, tert-butyl and pentyl, is preferred. The alkyl can be substituted or unsubstituted, and when substituted, the substituent can be halogen, nitro, sulfonyl, ether oxy, ether thio, ester, thioester or cyano.

The C₁-C₄ alkyl is linear or branched, comprising saturated hydrocarbon chain having 1 to 4 carbon atoms. It can be methyl, ethyl, propyl, isopropyl, butyl, isobutyl, sec-butyl or tert-butyl.

The "mixture of the enantiomers in all ratios" as used herein has the same meaning as the "mixture of the enantiomers in any ratio".

MODE OF CARRYING OUT THE INVENTION

Preparation of Compound 1

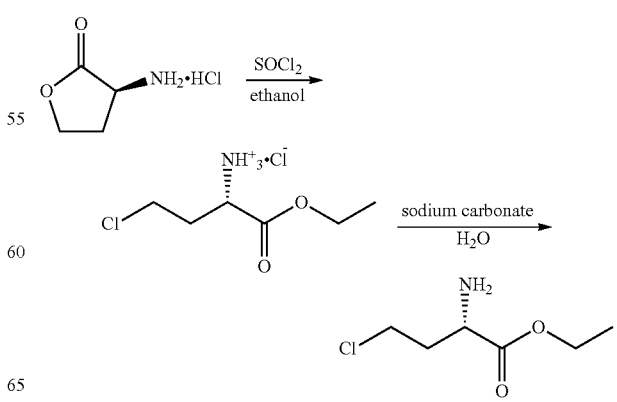

10 g of L-homoserine lactone hydrochloride (ee value of 99%, 137.56 g/mol, 0.073 mol) was weighed into a reaction flask, and 50 mL of ethanol (46.07 g/mol, 0.886 mol, 0.816 g/mL) was added (the molar ratio of homoserine lactone hydrochloride to ethanol is 1:12.1). The system was cooled to 10° C., and 21.7 g of thionyl chloride (118.97 g/mol, 0.182 mol) was slowly dropwise added (the molar ratio of L-homoserine lactone hydrochloride to thionyl chloride is 1:2.5). The system temperature was maintained at 10° C., and stirred for 30 minutes. The reaction was heated to 35° C., and stirred for 20 h, during which bubbles were continuously generated. The reaction was monitored by LC-MS. The reaction was stopped, the system was cooled to room temperature, and the remaining thionyl chloride and ethanol were distilled off under reduced pressure. The solid residue was slurried with 30 mL of n-hexane/ethyl acetate mixed solvents (the volume ratio of n-hexane to ethyl acetate is 2:1), filtered and dried to obtain 13.69 g of chloro-homoserine ethyl ester hydrochloride (202.08 g/mol, 0.0657 mol), wherein the HPLC purity is 97%, and the yield calculated on the basis of the amount of the reactant L-homoserine lactone hydrochloride is 90%.

The chloro-homoserine ethyl ester hydrochloride solid was reacted with a saturated sodium carbonate solution. The system was adjusted to a pH of 7-8, and extracted with ethyl acetate for 3 times, wherein the amounts of ethyl acetate in the 3 extraction processes were 30 mL, 10 mL and 10 mL, respectively. The organic phases were collected, and concentrated to obtain 10.30 g of the oily target product, chloro-homoserine ethyl ester (165.62 g/mol, 0.0591 mol), wherein the HPLC purity was 95%, the ee value was 99%, and the yield calculated based on the intermediate product chloro-homoserine ethyl ester hydrochloride was 90%.

MS (ESI): m/z [M+H]$^+$ calculated for C6H13ClNO2: 166.06, found: 166.0.

$^1$H NMR (CDCl$_3$, 400 MHz) δ: 4.04 (q, J=7.1 Hz, 2H), 3.65-3.50 (m, 2H), 3.48 (dd, J=9.0, 4.7 Hz, 1H), 2.05 (dddd, J=14.7, 8.5, 6.4, 4.6 Hz, 1H), 1.87-1.64 (m, 3H), 1.13 (t, J=7.2 Hz, 3H).

$^{13}$C NMR (CDCl$_3$, 100 MHz) δ: 175.3, 61.0, 51.6, 41.5, 37.0, 14.1.

Example 1

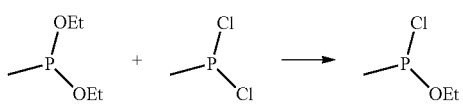

Under a nitrogen atmosphere, diethyl methylphosphonite (65.9 g, 484.8 mmol, 1.0 eq) and a solvent 1,4-dioxane (66 g) were added to a round-bottom flask, a 1,4-dioxane (63 g) solution of dichloro(methyl)phosphane (62.3 g, 533.3 mmol, 1.1 eq) were dropwise added through a constant-pressure funnel, and the reaction was stirred at room temperature overnight. 1,4-dioxane and chloro(ethoxy)(methyl)phosphane (colorless liquid, 85.8 g, yield: 70%) were distilled out under reduced pressure.

$^1$H NMR (D$_2$O, 43 MHz) δ: 3.92-2.96 (m, 2H), 1.31 (d, J=12.8 Hz, 3H), 0.84 (t, J=7.0 Hz, 3H).

Example 2

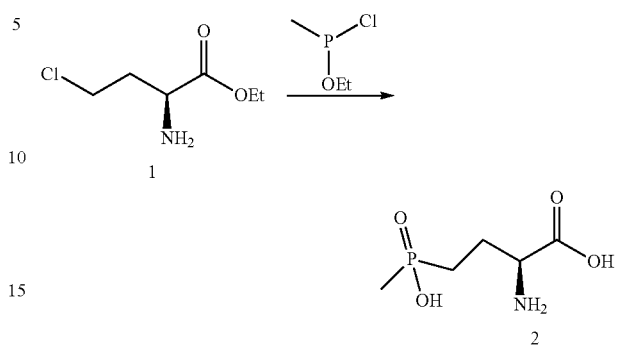

Under a nitrogen atmosphere, compound 1 (40.0 g, 242.4 mmol, 1.0 eq), chlorobenzene (81.9 g, 727.2 mmol, 3.0 eq) and triethylamine (29.4 g, 290.9 mmol, 1.2 eq) were respectively added to a three-neck flask, chloro(ethoxy)(methyl)phosphane (36.8 g, 290.9 mmol, 1.2 eq) was dropwise added, and the reaction was stirred at room temperature for 2 hours. The reaction was heated to 100° C., and allowed to proceed for 20 h. MS detection indicated that the raw material disappeared. The reaction was cooled to room temperature, dropwise added with 36% HCl (294.9 mL, 3432.6 mmol, 14.0 eq), and heated to reflux until complete reaction of the starting material. The solvent was evaporated, 95% ethanol (200 mL) and water (20 mL) were added, and the mixture was heated to reflux until the product was completely dissolved. The mixture was cooled and crystallized, filtered, and dried to obtain L-glufosinate (white crystal, 38.4 g, yield: 88%, 98% ee).

MS (ESI): m/z [M+H]$^+$ calculated for C5H13NO4P: 182.05, found 182.1.

$^1$H NMR (D$_2$O, 400 MHz) δ: 4.08 (t, J=6.2 Hz, 1H), 2.11 (dddd, J=14.6, 11.0, 8.7, 6.0 Hz, 2H), 1.99-1.73 (m, 2H), 1.44 (d, J=14.2 Hz, 3H).

$^{13}$C NMR (D$_2$O, 100 MHz) δ: 171.0, 52.8, 52.6, 25.5, 24.6, 22.6, 22.5, 13.9, 13.0.

$^{31}$P NMR (D$_2$O, 160 MHz) δ: 53.8.

Example 3

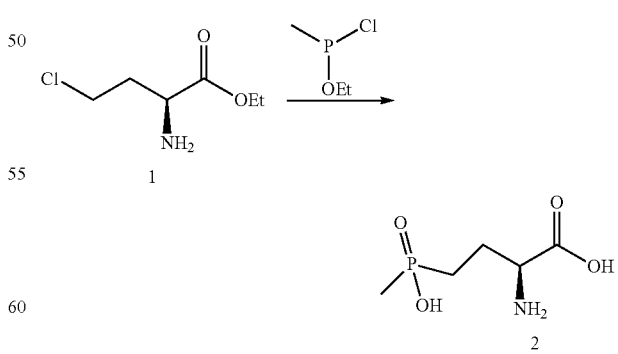

Under a nitrogen atmosphere, compound 1 (40.0 g, 242.4 mmol, 1.0 eq), chlorobenzene (81.9 g, 727.2 mmol, 3.0 eq) and pyridine (23.0 g, 290.9 mmol, 1.2 eq) were respectively added to a three-neck flask, chloro(ethoxy)(methyl)phosphane (36.8 g, 290.9 mmol, 1.2 eq) was dropwise added, and the reaction was stirred at room temperature for 2 hours. The reaction was heated to 100° C., and allowed to proceed for 20 h. MS detection indicated that the raw material disappeared. The reaction was cooled to room temperature, dropwise added with 36% HCl (294.9 mL, 3432.6 mmol, 14.0 eq), and heated to reflux until complete reaction of the starting material. The solvent was evaporated, 95% ethanol (200 mL) and water (20 mL) were added, and the mixture was heated to reflux until the product was completely dissolved. The mixture was cooled and crystallized, filtered, and dried to obtain L-glufosinate (white crystal, 35.3 g, yield: 81%, 96% ee).

Example 4

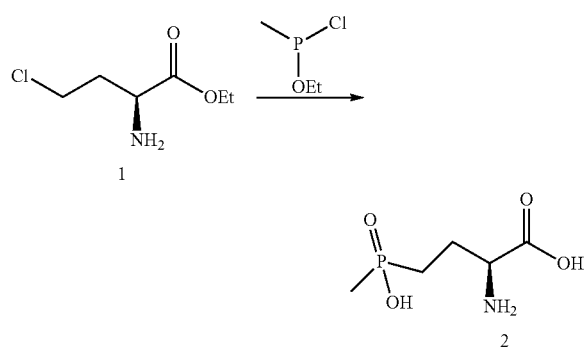

Under a nitrogen atmosphere, compound 1 (40.0 g, 242.4 mmol, 1.0 eq), chlorobenzene (81.9 g, 727.2 mmol, 3.0 eq) and piperidine (24.8 g, 290.9 mmol, 1.2 eq) were respectively added to a three-neck flask, chloro(ethoxy)(methyl) phosphane (36.8 g, 290.9 mmol, 1.2 eq) was dropwise added, and the reaction was stirred at room temperature for 2 hours. The reaction was heated to 100° C., and allowed to proceed for 20 h. MS detection indicated that the raw material disappeared. The reaction was cooled to room temperature, dropwise added with 36% HCl (294.9 mL, 3432.6 mmol, 14.0 eq), and heated to reflux until complete reaction of the starting material. The solvent was evaporated, 95% ethanol (200 mL) and water (20 mL) were added, and the mixture was heated to reflux until the product was completely dissolved. The mixture was cooled and crystallized, filtered, and dried to obtain L-glufosinate (white crystal, 33.2 g, yield: 76%, 94% ee).

Example 5

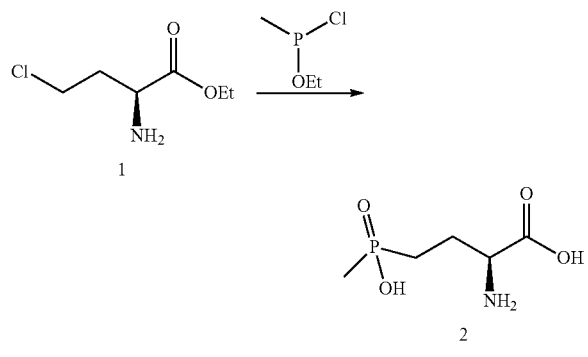

Under a nitrogen atmosphere, compound 1 (40.0 g, 242.4 mmol, 1.0 eq) and chlorobenzene (81.9 g, 727.2 mmol, 3.0 eq) were respectively added to a three-neck flask. Chloro(ethoxy)(methyl)phosphane (36.8 g, 290.9 mmol, 1.2 eq) was dropwise added, and ammonia was simultaneously bubbled in until saturation. The reaction was stirred at room temperature for 2 hours. The reaction was heated to 100° C., and allowed to proceed for 20 h. MS detection indicated that the raw material disappeared. The reaction was cooled to room temperature, dropwise added with 36% HCl (294.9 mL, 3432.6 mmol, 14.0 eq), and heated to reflux until complete reaction of the starting material. The solvent was evaporated, 95% ethanol (200 mL) and water (20 mL) were added, and the mixture was heated to reflux until the product was completely dissolved. The mixture was cooled and crystallized, filtered, and dried to obtain L-glufosinate (white crystal, 38 g, yield: 87%, 97% ee).

Example 6

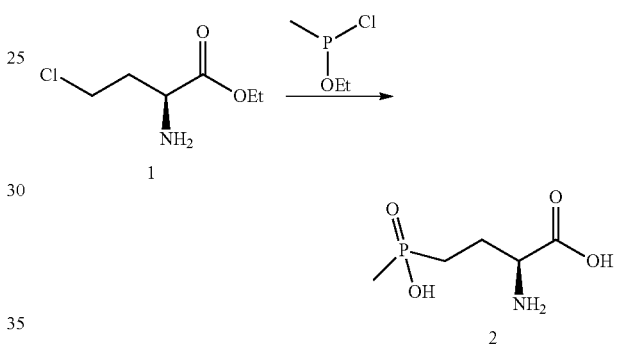

Under a nitrogen atmosphere, compound 1 (40.0 g, 242.4 mmol, 1.0 eq), 1,4-dioxane (64 g, 727.2 mmol, 3.0 eq) and triethylamine (29.4 g, 290.9 mmol, 1.2 eq) were respectively added to a three-neck flask, chloro(ethoxy)(methyl)phosphane (36.8 g, 290.9 mmol, 1.2 eq) was dropwise added, and the reaction was stirred at room temperature for 2 hours. The reaction was heated to 100° C., and allowed to proceed for 20 h. MS detection indicated that the raw material disappeared. The reaction was cooled to room temperature, dropwise added with 36% HCl (294.9 mL, 3432.6 mmol, 14.0 eq), and heated to reflux until complete reaction of the starting material. The solvent was evaporated, 95% ethanol (200 mL) and water (20 mL) were added, and the mixture was heated to reflux until the product was completely dissolved. The mixture was cooled and crystallized, filtered, and dried to obtain L-glufosinate (white crystal, 36.2 g, yield: 83%, 97% ee).

Example 7

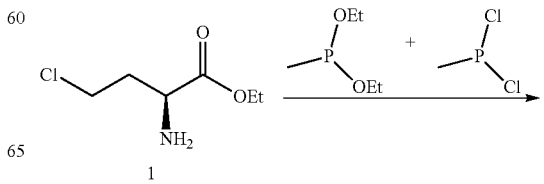

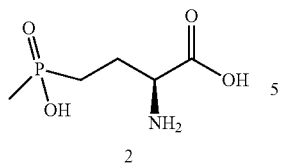

2

Under a nitrogen atmosphere, dichloro(methyl)phosphane (520.5 mmol, 0.6 eq, purity: 90%) was added to a round-bottom flask at room temperature (20° C.), diethyl methylphosphonite (1735 mmol, 2.0 eq, purity: 98%) was dropwise added through a constant-pressure funnel, and the reaction was continuously stirred for 10 minutes after the dropwise addition. A solution of compound 1 (867.5 mmol, 1.0 eq, purity: 96%, ee value: 99%) and triethylamine (107.5 g, 1041 mmol, 1.2 eq, purity: 98%) in 1,4-dioxane (500 g) was dropwise added, and the reaction was continuously stirred for 1.5 hours after the dropwise addition. The reaction solution was then heated to 90° C., and allowed to proceed for 20 h. The reaction solution was cooled to room temperature, and filtered with suction, the filter cake was washed with 1,4-dioxane (150 mL*3), and the filtrate was rotary evaporated to remove 1,4-dioxane. The reaction was added with 100 mL of concentrated hydrochloric acid (36%), heated to 90° C., and allowed to proceed for 10 hours. The solvent was rotary evaporated to dryness, 200 mL of concentrated hydrochloric acid (36%) was supplemented, and the reaction was continued at 90° C. for 10 hours. MS detection indicated the intermediate disappeared, and analysis of the reaction solution at this time indicated that the enantiomeric excess percentage (% ee) of L-glufosinate in the reaction solution was 92%. The reaction solution was cooled to room temperature, rotary evaporated to remove the solvent, added with 95% ethanol (300 mL), and heated to reflux until the crude product was completely dissolved. The mixture was cooled and crystallized, filtered, and dried to obtain the compound of L-glufosinate (yield: 69%, 97% ee).

In addition to those described herein, according to the foregoing description, various modifications to the present invention would be apparent to those skilled in the art. Such modifications are intended to fall within the scope of the appended claims. Each reference cited herein (including all patents, patent applications, journal articles, books and any other disclosures) are incorporated herein by reference in its entirety.

What is claimed is:

1. A method for preparing glufosinate of formula (I);

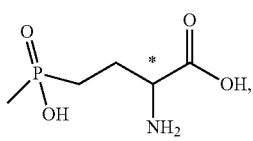

or a salt, an enantiomer or a mixture of enantiomers thereof, the method comprising steps of:

a) reacting a compound of formula (II):

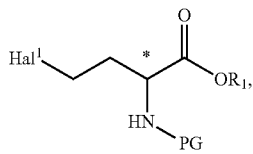

or a salt, an enantiomer or a mixture of enantiomers thereof,
with one or more compounds of formula (III) or a mixture to form an intermediate, the mixture comprising:
one or more compounds of the formula (IV) and one or more compounds of formula (V);
one or more compounds of the formula (IV) and one or more compounds of the formula (III);
one or more compounds of formula (V) and one or more compounds of the formula (III); or
one or more compounds of the formula (III), one or more compounds of the formula (IV) and one or more compounds of the formula (V)

b) reacting the intermediate, isolated or not isolated, in the presence of water and an acid or a base to obtain the glufosinate of the formula (I) or the salt, the enantiomer or the mixture of enantiomers thereof,
wherein when PG is an amino protecting group, the method further comprises a step of removing the amino protecting group, and
wherein:
$Hal^1$ and $Hal^2$ are each independently halogen;
PG is hydrogen or an amino protecting group;
$R_1$, $R_2$, $R_3$ and $R_4$ are each independently alkyl, phenyl or substituted phenyl, and when the mixture comprises one or more compounds of the formula (IV) and one or more compounds of the formula (III), or when the mixture comprises one or more compounds of the formula (III), one or more compounds of the formula (IV) and one or more compounds of the formula (V), $R_2$ is either $R_3$ or $R_4$; and
the chiral carbon atom is labeled with *.

2. The method according to claim 1, wherein the compound of the formula (II) in the step a) is enantiomerically pure.

3. The method according to claim 1, wherein an enantiomeric ratio is (L):(D)-enantiomer or (D):(L)-enantiomer of 50.5:49.5 to 99.5:0.5.

4. The method according to claim 3, wherein the enantiomeric ratio is (L):(D)-enantiomer of 50.5:49.5 to 99.5:0.5.

5. The method according to claim 1, wherein PG is hydrogen.

6. The method according to claim 1, wherein $Hal^1$ is a chlorine atom.

7. The method according to claim 1, wherein $Hal^2$ is a chlorine atom.

8. The method according to claim 1, wherein $R_1$, $R_2$, $R_3$ and $R_4$ are each independently $C_1$-$C_6$ alkyl.

9. The method according to claim 1, wherein $R_1$ is ethyl.

10. The method according to claim 1, wherein $R_2$ is ethyl.

11. The method according to claim 1, wherein $R_3$ is ethyl.

12. The method according to claim 1, wherein $R_4$ is ethyl.

13. The method according to claim 1, wherein the mixture comprises:
   one or more compounds of the formula (IV) and one or more compounds of the formula (III), and a molar ratio of the compounds of the formula (IV) to the compounds of the formula (III) is (0.9-1.1):1 or (0.05-1.1):1;
   one or more compounds of the formula (V) and one or more compounds of the formula (III), and a molar ratio of the compounds of the formula (V) to the compounds of the formula (III) is (0.9-1.1):1 or (0.05-1.1):1; or
   one or more compounds of the formula (IV) and one or more compounds of the formula (V), and a molar ratio of the compounds of the formula (IV) to the compounds of the formula (V) is (0.9-1.1):1.

14. The method according to claim 1, wherein in the step a), reaction temperature is 20 to 200° C.

15. The method according to claim 1, wherein the step a) is carried out in the presence of a base.

16. The method according to claim 15, wherein the base in the step a) is an organic base or ammonia.

17. The method according to claim 16, wherein in the step a), the organic base is selected from the group consisting of an organic amine, pyridine or a pyridine derivative having 1-3 substituents attached to one or more carbon atoms in a heterocycle, and piperidine or a piperidine derivative having 1-3 substituents attached to one or more carbon atoms in a heterocycle.

18. The method according to claim 17, wherein the organic base comprises triethylamine, piperidine or pyridine.

19. The method according to claim 1, wherein in the step a), a molar ratio of a base to total amounts of the compound of the formula (III) and the compound of the formula (V) is (1-10):1.

20. The method according to claim 1, wherein the step a), the reaction is carried out under a solvent-free condition or in an inert solvent.

21. The method according to claim 20, wherein in the step a), the inert solvent is selected from one or more of benzene solvents, amide solvents, hydrocarbon solvents, halogenated hydrocarbon solvents, sulfone solvents, sulfoxide solvents, ether solvents, and ester solvents.

22. The method according to claim 21, wherein in the step a), the inert solvent is selected from one or more of chlorobenzene, trimethylbenzene, 1,4-dioxane, 1,2-dichloroethane, dimethyl sulfoxide, N-methylpyrrolidone, N,N-dimethylformamide, petroleum ether, n-heptane, tetrahydrofuran, methyltetrahydrofuran, benzene, toluene, ethyl acetate, and butyl acetate.

23. The method according to claim 1, wherein in the step a), a molar ratio of the compound of the formula (III) or the mixture to the compound of the formula (II) is 1:(0.8-10); or a molar ratio of the compound of the formula (II) to the compound of the formula (III) or the mixture is 1:(0.8-10).

24. The method according to claim 1, wherein in the step b), an inorganic acid or an organic acid is added.

25. The method according to claim 24, wherein the inorganic acid is hydrochloric acid or sulfuric acid.

26. The method according to claim 1, wherein in the step b), the base is an inorganic base or an organic base.

27. The method according to claim 26, wherein the base is alkali metal hydroxide, alkali-earth metal hydroxide, alkali metal carbonate, alkali-earth metal carbonate, alkali metal bicarbonate or alkali-earth metal bicarbonate.

28. The method according to claim 27, wherein the base is NaOH, KOH or $Ba(OH)_2$.

29. The method according to claim 1, wherein in the step b), reaction temperature is 20 to 150° C.

30. A method for preparing L-glufosinate or a salt thereof, wherein a compound of formula (IIa) is reacted with a compound of formula (IIIa):

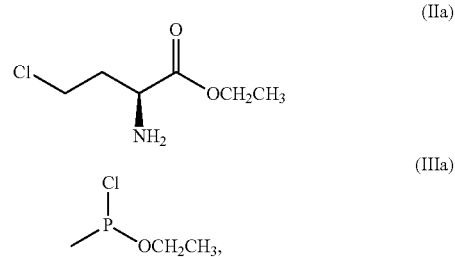

and an acid is then added to obtain the L-glufosinate or the salt thereof.

31. The method according to claim 1, wherein the compound of formula (III) is a compound of formula (IIIa):

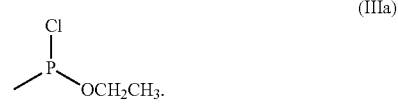

* * * * *